United States Patent
Weir et al.

(10) Patent No.: US 7,558,455 B2
(45) Date of Patent: Jul. 7, 2009

(54) RECEIVER APERTURE BROADENING FOR SCANNED BEAM IMAGING

(75) Inventors: Michael P. Weir, Blanchester, OH (US); John R. Lewis, Bellevue, WA (US); Amjad I. Malik, Bothell, WA (US); Christopher A. Wiklof, Everett, WA (US); Mathew D. Watson, Bellevue, WA (US); Richard A. James, Woodinville, WA (US)

(73) Assignees: Ethicon Endo-Surgery, Inc, Cincinnati, OH (US); Microvision, Inc., Redmond, WA (US)

( * ) Notice: Subject to any disclaimer, the term of this patent is extended or adjusted under 35 U.S.C. 154(b) by 0 days.

(21) Appl. No.: 11/770,849

(22) Filed: Jun. 29, 2007

(65) Prior Publication Data

US 2009/0002794 A1    Jan. 1, 2009

(51) Int. Cl.
*G02B 6/06* (2006.01)
(52) U.S. Cl. ...................... 385/119; 385/116
(58) Field of Classification Search .......... 385/115–121
See application file for complete search history.

(56) References Cited

U.S. PATENT DOCUMENTS

| | | | |
|---|---|---|---|
| 3,758,199 A | 9/1973 | Thaxter | |
| 3,959,582 A | 5/1976 | Law et al. | |
| 4,409,477 A * | 10/1983 | Carl | 250/227.26 |
| 4,803,550 A | 2/1989 | Yabe et al. | |
| 4,902,115 A | 2/1990 | Takahashi | |
| 5,200,819 A | 4/1993 | Nudelman et al. | |
| 5,207,670 A | 5/1993 | Sinofsky | |
| 5,218,195 A | 6/1993 | Hakamata | |
| 5,251,613 A | 10/1993 | Adair | |
| 5,269,289 A | 12/1993 | Takehana et al. | |
| 5,436,655 A | 7/1995 | Hiyama et al. | |
| 5,531,740 A | 7/1996 | Black | |
| 5,608,451 A | 3/1997 | Konno et al. | |
| 5,768,461 A | 6/1998 | Svetkoff et al. | |
| 6,056,721 A | 5/2000 | Shulze et al. | |
| 6,059,720 A | 5/2000 | Furusawa et al. | |

(Continued)

FOREIGN PATENT DOCUMENTS

DE    3837248    5/1990

(Continued)

OTHER PUBLICATIONS

Ra, H. et al., "Biomedical Optics & Medical Imaging—Microtechnology enables endoscopic confocal microscopy," SPIE (http://spie.org) (2007).

(Continued)

*Primary Examiner*—Charlie Peng
(74) *Attorney, Agent, or Firm*—Victor Moreno (57) ABSTRACT

A scanning beam assembly includes a beam generator to generate a beam of radiation; at least one reflector configured to deflect the beam across a field of view; and a plurality of multi-mode optical fibers for receiving radiation reflected from the field of view, wherein the optical fibers have end surfaces that face in at least two different directions, or wherein the optical fibers are configured to receive scattered radiation from an angular field of view larger than that determined by their individual numerical apertures.

28 Claims, 12 Drawing Sheets

U.S. PATENT DOCUMENTS

| | | |
|---|---|---|
| 6,178,346 B1 | 1/2001 | Amundson et al. |
| 6,192,267 B1 | 2/2001 | Scherninski et al. |
| 6,210,401 B1 | 4/2001 | Lai |
| 6,276,798 B1 | 8/2001 | Gil et al. |
| 6,327,493 B1 | 12/2001 | Ozawa et al. |
| 6,370,406 B1 * | 4/2002 | Wach et al. .................. 600/310 |
| 6,445,362 B1 | 9/2002 | Tegreene |
| 6,462,770 B1 | 10/2002 | Cline et al. |
| 6,529,770 B1 | 3/2003 | Grimblatov |
| 6,530,698 B1 | 3/2003 | Kuhara et al. |
| 6,572,606 B2 | 6/2003 | Kliewer et al. |
| 6,741,884 B1 | 5/2004 | Freeman et al. |
| 6,902,527 B1 | 6/2005 | Doguchi et al. |
| 6,975,898 B2 | 12/2005 | Seibel et al. |
| 6,991,602 B2 * | 1/2006 | Nakazawa et al. .......... 600/113 |
| 7,189,961 B2 | 3/2007 | Johnston et al. |
| 7,232,071 B2 * | 6/2007 | Lewis et al. ............... 235/462.1 |
| 7,271,383 B2 | 9/2007 | Chee |
| 7,391,013 B2 | 6/2008 | Johnston et al. |
| 2002/0115922 A1 | 8/2002 | Waner et al. |
| 2003/0034709 A1 | 2/2003 | Jerman |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0225222 A1 | 11/2004 | Zeng et al. |
| 2005/0014995 A1 | 1/2005 | Amundson et al. |
| 2005/0020877 A1 | 1/2005 | Ishihara et al. |
| 2005/0020926 A1 | 1/2005 | Wiklof et al. |
| 2005/0023356 A1 | 2/2005 | Wiklof et al. |
| 2005/0116038 A1 * | 6/2005 | Lewis et al. .................. 235/454 |
| 2005/0162762 A1 | 7/2005 | Novak |
| 2005/0187441 A1 | 8/2005 | Kawasaki et al. |
| 2005/0203343 A1 | 9/2005 | Kang et al. |
| 2006/0195014 A1 | 8/2006 | Seibel et al. |
| 2006/0238774 A1 | 10/2006 | Lindner et al. |
| 2007/0046778 A1 | 3/2007 | Ishihara et al. |
| 2007/0156021 A1 | 7/2007 | Morse et al. |
| 2007/0161876 A1 | 7/2007 | Bambot et al. |
| 2007/0162093 A1 | 7/2007 | Porter et al. |
| 2007/0167681 A1 | 7/2007 | Gill et al. |
| 2007/0173707 A1 | 7/2007 | Mitra |
| 2007/0179366 A1 | 8/2007 | Pewzner et al. |
| 2007/0197874 A1 | 8/2007 | Ishihara |
| 2007/0197875 A1 | 8/2007 | Osaka |
| 2007/0203413 A1 | 8/2007 | Frangioni |
| 2007/0213588 A1 | 9/2007 | Morishita et al. |
| 2007/0213618 A1 | 9/2007 | Li et al. |
| 2007/0225695 A1 | 9/2007 | Mayer et al. |
| 2007/0238930 A1 | 10/2007 | Wiklof et al. |
| 2007/0244365 A1 | 10/2007 | Wiklof |
| 2008/0058629 A1 | 3/2008 | Seibel et al. |

FOREIGN PATENT DOCUMENTS

| | | |
|---|---|---|
| EP | 1139141 | 10/2001 |
| EP | 1747751 | 1/2007 |
| EP | 1797813 | 6/2007 |
| JP | 2007-244590 | 9/2007 |
| JP | 2007-244680 | 9/2007 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | 03/088643 | 10/2003 |
| WO | 03/098918 | 11/2003 |
| WO | 03/101287 | 11/2003 |
| WO | 03/101287 | 12/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

International Search Report issued regarding International Application No. PCT/US2007/078868 (Mar. 28, 2008).

PCT, International Search Report, PCT/US2008/056589 (Jul. 30, 2008).

PCT, International Search Report, PCT/US2008/059231 (Jul. 4, 2008).

PCT, International Search Report, PCT/US2007/087923 (May 21, 2008).

PCT, International Search Report, PCT/US2008/056596 (Jun. 23, 2008).

PCT, International Search Report, PCT/US2008/059235 (Jul. 14, 2008).

PCT, International Search Report, PCT/US2007/087930 (Jul. 3, 2008).

PCT, International Search Report, PCT/US2008/051274 (Jul. 18, 2008).

PCT, International Search Report, PCT/US2008/066552 (Oct. 23, 2008).

Invitation to Pay Additional Fees with Partial International Search Report, PCT/US2008/074275 (Jan. 16, 2009).

Invitation to Pay Additional Fees with Partial International Search Report, PCT/US2008/074273 (Dec. 30, 2008).

International Search Report, PCT/US2008/066552 (Oct. 23, 2008).

* cited by examiner

RECEIVER APERTURE BROADENING FOR SCANNED BEAM IMAGING

TECHNICAL FIELD

The present disclosure is related generally to a scanned beam assembly adapted for imaging, and more particularly to a scanned beam assembly having light collectors with improved detection sensitivity at selected incident angles across a field of view.

BACKGROUND OF THE INVENTION

Figure 1:
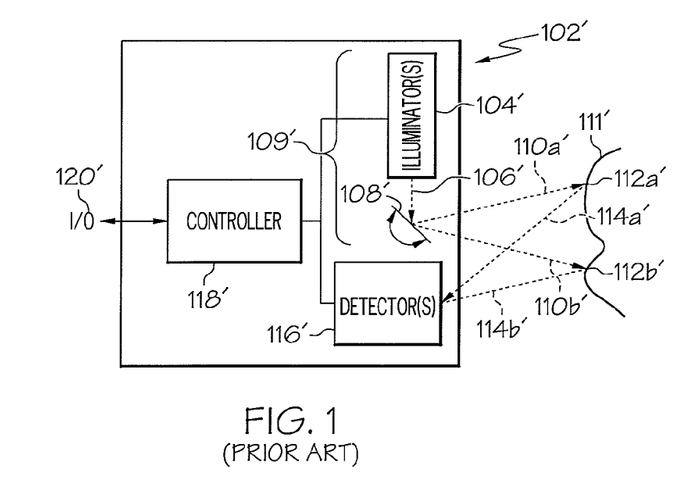
FIG. 1 is a schematic illustration of a scanning beam imager, according to an embodiment.

U.S. Published Application 2005/0020926A1, incorporated by reference herein, discloses a scanning beam imager which is reproduced in FIG. 1 herein. The imager may be used in applications in which cameras have been used in the past. In particular it may be used in medical devices such as video endoscopes, laparoscopes, etc.

FIG. 1 shows a block diagram of one example of a scanned beam imager 102'. An illuminator 104' creates a first beam of light 106'. A scanner 108' deflects the first beam of light across a field-of-view (FOV) 111' to produce a second scanned beam of light 110', shown in two positions 110'a and 110'b. The illuminator 104', first beam of light 106' and scanner 108' assembly may be generally designated 109'. The scanned beam of light 110' sequentially illuminates spots 112' in the FOV 111', shown as positions 112'a and 112'b, corresponding to beam positions 110'a and 110'b, respectively. While the beam 110' illuminates the spots 112', the illuminating light beam 110' is reflected, absorbed, scattered, refracted, or otherwise affected by the object or material in the FOV 111' to produce scattered light energy. A portion of the scattered light energy 114', shown scattered from spot positions 112'a and 112'b as scattered energy rays 114'a and 114'b, respectively, travels to one or more detectors 116' that receive the light and produce electrical signals corresponding to the amount of light energy received. Image information is provided as a serial data stream, where locations in the data stream correspond to positions in the scan pattern. The electrical signals may be transmitted to an image processor 118' that assembles the values in the data stream into a digital image. The image processor 118' may transmit the digital image for further processing, decoding, archiving, printing, display, or other treatment or use via interface 120'.

Illuminator 104' may include multiple emitters such as, for instance, light emitting diodes (LEDs), lasers, thermal sources, arc sources, fluorescent sources, gas discharge sources, or other types of illuminators. Illuminator 104' may include, in the case of multiple emitters, beam combining optics to combine some or all of the emitters into a single beam. Illuminators 104' may also include beam-shaping optics such as one or more collimating lenses and/or apertures. Light beam 106', while illustrated as a single beam, may comprise a plurality of beams converging on a single scanner 108' or onto separate scanners 108'.

In a scanned beam imager (SBI), a beam director may be formed as a scanning reflector or reflectors operable to oscillate in periodic motion to reflect a beam of light in a periodic pattern. According to an embodiment, a beam director may be formed as a resonant device. According to an embodiment, a beam director may be driven to oscillate such that its velocity varies approximately sinusoidally in time and across a corresponding periodic scan pattern. One example of a beam director comprises a MEMS scanner capable of periodic deflection at a frequency near a mechanical resonant frequency. The resonant frequency may be determined by the torsional or bending stiffness of a torsion arm or cantilever arm, the moment of inertia of the oscillating body incorporating the reflector, and/or other factors such as material stiffness, processing parameters, device temperature, ambient pressure, etc.

In one example, a MEMS scanner oscillates about two scan axes that may be orthogonal. In an example, one axis is operated near resonance while the other is operated substantially off resonance. Such a case may include, for example, the nonresonant axis being driven to achieve a triangular or a sawtooth velocity profile. In another example, both axes may be operated near different resonant frequencies to produce, for example, a Lissajous scan pattern.

Figure 2:
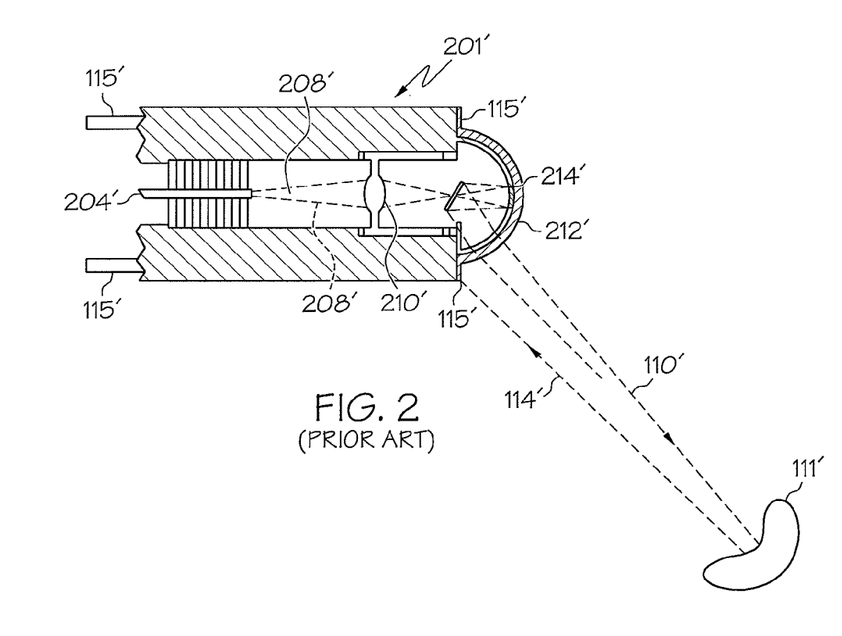
FIG. 2 is a schematic diagram of an optical system, according to an embodiment.

As illustrated in FIG. 2, a scanned beam source 201' may comprise a meniscus objective lens or dome 212' having a reflective surface 212'. The reflective surface 214' may be integral to the dome 212', such as located on the lens surface as shown in FIG. 2, or it may be suspended from or mounted on the incident side of the dome. The dome 212' optionally has optical power and shapes and/or refracts the scanned beam 110' as it passes through the dome. The beam 208' emitted from the optical fiber 204' is directed to the reflector 214' via a shaping optic 210'. As shown in FIG. 1, a portion of the radiation reflected/scattered from the FOV 111', travels to one or more detectors that receive the light and transmit it to a detector element 116' that produces electrical signals corresponding to the amount of light energy received. The receiving fiber array 115' may comprise an annular bundle of fine optical fibers generally oriented parallel to the central axis of the SBI.

It has been observed that the corners and edges of the FOV 111' in exemplary devices may be relatively dark, even in systems where the illuminating beam 110' dwells in these regions for a longer time as a result of the sinusoidal angular deflecting movement of a resonant mirror 108'. This darkening may be associated both with lack of detection sensitivity at wide angles and/or the $\cos^n$ falloff of illumination in an optical system.

SUMMARY OF THE INVENTION

According to an embodiment, a scanning beam assembly includes a beam generator to generate a beam of radiation; at least one beam director configured to direct the beam across a field of view in a periodic pattern; and a plurality of multi-mode optical fibers for receiving radiation scattered from the field of view, wherein the optical fibers have end surfaces that face in at least two different directions.

In another aspect, the plurality of fibers is a fiber bundle having a longitudinal axis and includes a first group of fibers that form a core of the fiber bundle and at least one additional group of fibers that form an annulus or region surrounding the core wherein the end surfaces of the fibers in the core and the end surfaces of the fibers in the annulus face different directions.

In another aspect, the plurality of fibers may be a fiber bundle having an end surface configured to broaden the sensitivity or increase the numerical aperture of the fibers. According to an embodiment, the end surface may be coated with a diffusive material containing reflective particles that direct light to the end surface of the fiber from different areas of the field of view. According to another embodiment, a layer of poly-tetra-fluoro-ethylene (PTFE) or other numerical aperture increasing material may be placed over the end surface of the fiber bundle. According to an embodiment, angled fiber tips may be combined with use of a diffusive layer.

In yet another aspect, the plurality of fibers include fibers splayed such that their end surfaces face two or more different areas within the field of view to receive radiation from different areas within the field of view.

Other aspects according to embodiments will become apparent from the following detailed description, the accompanying drawings and the appended claims.

DETAILED DESCRIPTION OF THE INVENTION

Before describing the disclosed scanning beam assembly in detail, it should be noted that the disclosure is not limited in its application or use to the details of construction and arrangement of parts illustrated in the accompanying drawings and description. The illustrative embodiments may be implemented or incorporated in other embodiments, variations and modifications, and may be practiced or carried out in various ways. Furthermore, unless otherwise indicated, the terms and expressions employed herein have been chosen for the purpose of describing the illustrative embodiments for the convenience of the reader and are not intended to be limiting.

Figure 3:
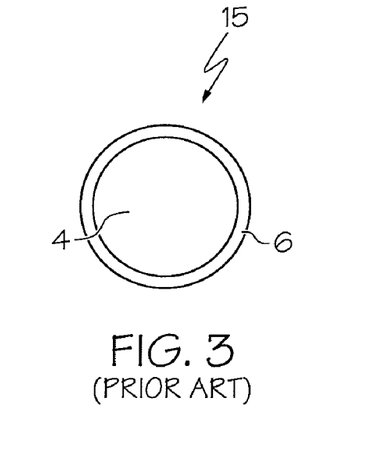
FIG. 3 is a end view of an optical fiber, according to an embodiment.

A step index optical fiber, generally designated 15 in FIG. 3, typically includes a core 4, and a cladding layer 6. The optical fiber 15 is a filament of transparent dielectric material that guides light using substantially total internal reflection. The core 4 is surrounded by, and is in intimate contact with, the cladding 6 of similar geometry. The optical fiber 15 may be of various cross-sectional shapes, for example, circular, square, rectangular, etc. Such structure allows the core 4 to carry optical information and allows the cladding 6 to provide an optical boundary, reflecting the light back to the core 4. This reflection is accomplished by the cladding 6 having a refractive index that is lower than the refractive index of the core 4 so that light can be guided by the optical fiber 15 in accordance with Snell's law.

Figure 4:
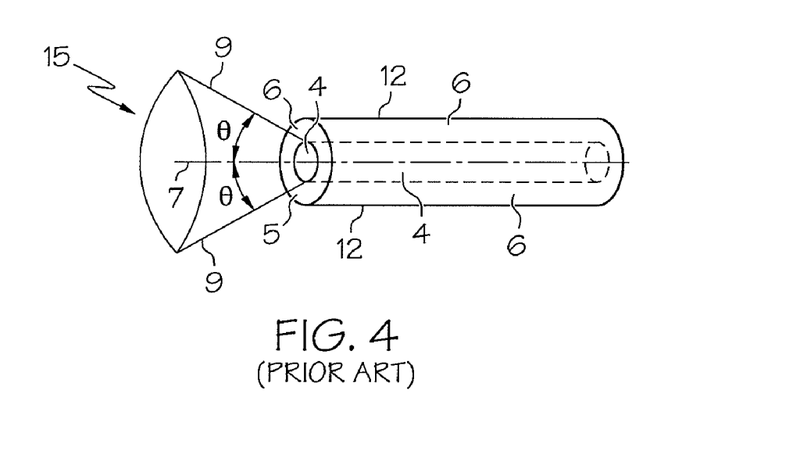
FIG. 4 is a side perspective view of the fiber of FIG. 3, illustrating the acceptance cone for light entering the fiber, according to an embodiment.

Referring to FIG. 4, an optical fiber 15 having a end face disposed perpendicular to its longitudinal axis, will only propagate light that enters the end face 5 within a cone 9 referred to as the acceptance cone of the fiber 15. The half-angle of this cone is called the acceptance angle, $\theta_{max}$, as illustrated in FIG. 4. $\theta_{max}$ may be defined as the maximum angle at which light incident to the end of the fiber will be propagated down the fiber. Another way of expressing the fiber's acceptance angle, $\theta_{max}$, in terms of its numerical aperture (NA), which for light entering a fiber 15 from air is approximately $NA=(n_o^2-n_1^2)^{1/2}$, where $n_o$ is the refractive index of the core and $n_1$, is the index of the cladding. An alternate but equivalent definition is $NA=\sin(\theta_{max})$. Single-mode optical fibers may be characterized by relatively small NA acceptance angles. Multi-mode optical fibers may be characterized by relatively large NA acceptance angles. For scanned beam imaging systems having relatively large angular fields of view, it may be preferable to use multi-mode optical fibers as collection fibers.

Figure 5:
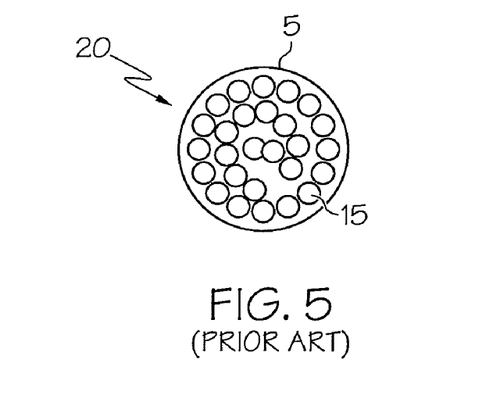
FIG. 5 is a end view of an optical fiber bundle, according to an embodiment.

According to an embodiment, a bundle comprising a plurality of optical fibers may be used to collect light. A light collecting fiber bundle, generally designated 20, as shown in FIG. 5, may contain several to many thousands of fibers 15. Methods of making fiber bundles 20 are known in the art. Neither light that impinges on the end surface 5 of the fiber from an angle that is outside the acceptance cone nor light that impinges outside the core 4, for example impinging upon the cladding 6, are transmitted by the fiber. Most light entering the cladding is lost, which can limit fiber transmission efficiency. This makes the fraction of the surface made up by fiber cores an important factor in a bundle's light collection efficiency. The collection efficiency depends (in part) on the packing fraction defined as the ratio of the total core area to the total surface area.

In accordance with an embodiment, fibers are used having one or more end surfaces that face in different directions. The term "face" as used herein with respect to the end surfaces means the direction that a line extending perpendicular from the end face points. Accordingly, in one embodiment the end surfaces of two or more fibers face in different directions. In one embodiment the angle between the perpendiculars to the end faces of two or more faces is at least about 5 degrees and, more particularly, at least about 10 degrees. According to an embodiment, fiber ends of about 0.66 NA multi-mode optical fibers may be cut or cleaved at an angle of about 13.7 degrees to produce about a 70 degree from axial maximum collection angle.

The term "faceted surface" as used herein with respect to the end surfaces means a surface including two or more flat planes. In one embodiment, faceted surfaces include but are not limited to multi-faceted surfaces, etc. One example of a multi-faceted surface is shown in FIG. 7C.

Alternative shapes for the fiber bundle end surface include but are not limited to multi-faceted surface, parabolic end surface, hemispherical surface, etc. They may or may not be rotationally symmetrical (i.e., figures of revolution). The shape of the end surface is such as to broaden the limits of the acceptance cone in which light is accepted. Alternative shapes for the fiber bundle end surface may be generated using any convenient method, such as but not limited to polishing a fiber bundle, laser etching a fiber bundle, chemically etching a fiber bundle, etc.

Figure 6A:
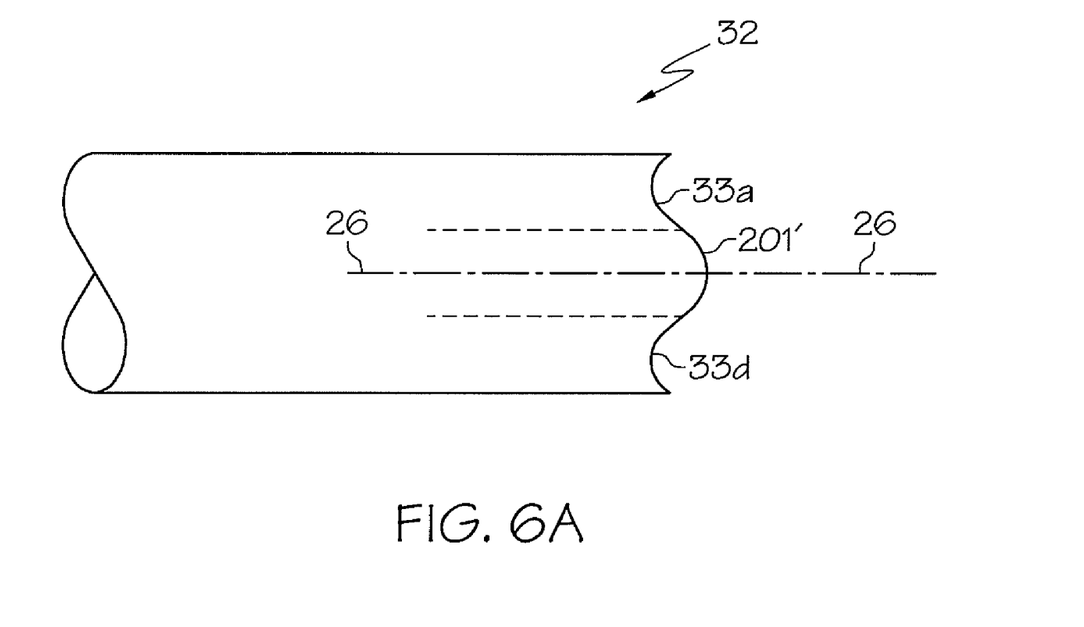
FIG. 6A is a side perspective view of a conical fiber bundle end surface, surrounding a scanned beam source, according to an embodiment.
Figure 6B:
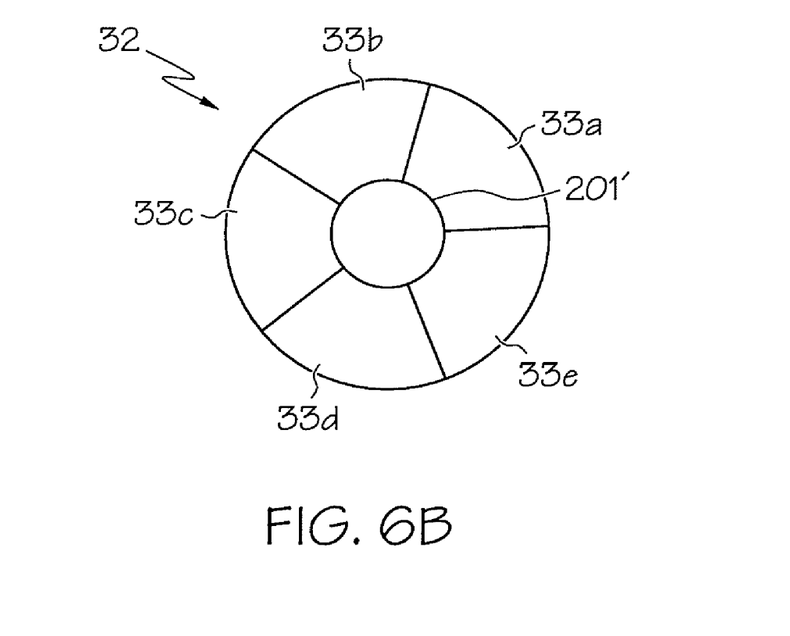
FIG. 6B is a end view of FIG. 6A illustrating a faceted fiber bundle end surface, according to an embodiment.

In another embodiment as shown in FIGS. 6A and 6B, a collection fiber bundle 32 may have a faceted end face 33a-33e and a longitudinal axis 26. The number of facets in the end face may vary from 2 to 12 in one embodiment of the invention. In the embodiment shown in FIG. 6B there are 5 facets 33a-33e on the end face 33. Each facet 33a-33e includes fibers in which the fibers in each facet face a different direction from those in other facets. Of course, the end faces 33 need not be uniformly oriented. For certain applications a nonuniform orientation of the end faces 33 may be advantageous. In operation, the scanned beam source 201' may scan a beam of light in a periodic pattern across a field of view. Light scattered from the flying spot produced the field of view may be collected by the collection fiber bundle 32. While the scanned beam source 201' is shown in schematic form as a block near the collection fiber bundle 32, the spatial relationship between the scanned beam source and the collection fiber bundle may be varied. According to an embodiment, the collection fiber bundle 32 may be configured to be circumjacent the scanned beam source 201'. According to another embodiment, the collection fiber 32 may be configured to be adjacent or side-by side with the scanned beam source 201'.

Figure 7A:
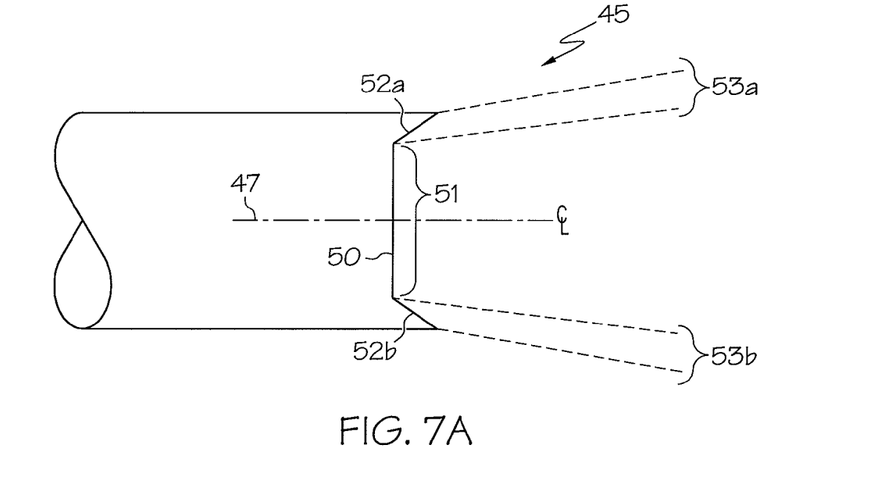
FIG. 7A is a side view of a fiber bundle including an angled end face having a polygonal surface, according to an embodiment.

In another embodiment as illustrated in FIG. 7A, a collection end 50 of a fiber bundle 45 may have a shape including a plurality of angles. For example, the end surface 50 may include a first angle across a first portion 51 of the end, and a second angle across second portions 52a, 52b of the end. According to the illustrative embodiment, the first portion 51 is shaped to have a flat surface aligned perpendicular to the axis 47 of the optical fiber bundle 45. The second portions 52a, 52b are shaped to have respective angles relative to the first portion 51.

Figure 7B:
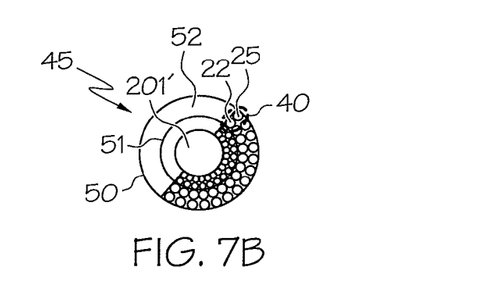
FIG. 7B is a partial cut-away end view of FIG. 7A showing a group of fibers that in combination form a core and at least one additional group of fibers that in combination form an annulus surrounding the core, according to an embodiment.
Figure 7C:
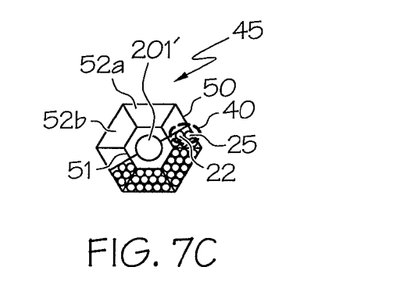
FIG. 7C is a partial cut-away end view of FIG. 7A showing a group of fibers that in combination form an angled tip core and at least one additional group of fibers that in combination form an angled annulus surrounding the core, according to an embodiment.

Referring to FIG. 7B, the end 50 of the fiber bundle 45 may include angled portions configured as concentric rings. The central area 51 of the fiber bundle end 50 may be surrounded by an annular area 52 having an angled face. Thus, comparing FIG. 7B to FIG. 7A, the areas 52a, 52b of FIG. 7a are formed as a continuous annular surfaces. The central area 51 may, in turn, be formed around a central scanning mechanism 201' such as that depicted in FIGS. 7B and 7C.

Another embodiment of the formation of the fiber bundle angles of FIG. 7A may be seen in FIG. 7C. In the illustrative embodiment of FIG. 7C, the central area 51 of the fiber bundle end 50 is in the form of a hexagon. Peripheral regions 52a, 52b are raised from points abutting the edges of the hexagonal flat surface 51 at angles that may be seen in FIG. 7A. The angled surfaces 52a, 52b may form tetrahedrons as indicated, may include radiused outer edges, or form other shapes. Of course, a shape other than hexagonal may be selected for the flat surface 51 and/or the outer periphery of the raised surfaces 52.

Figure 7D:
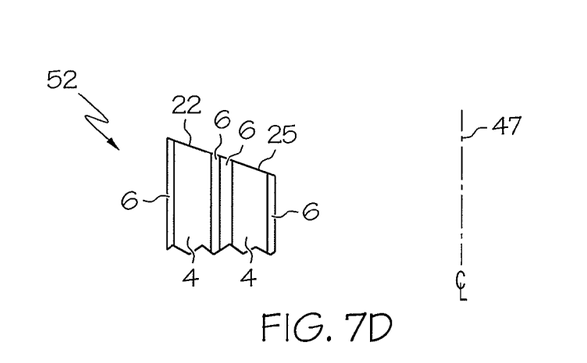
FIG. 7D is a sectional view of the fiber bundles of FIGS. 7B and 7C showing a diminishing height of successive fibers toward the peripheral edge of the annulus, according to an embodiment.

Referring to FIG. 7D, according to embodiments, the height of successive fibers 22, 25 within the angled areas 52, 52a, 52b (also shown in FIGS. 7A-7C) may decrease toward the centerline 47, or alternatively may decrease toward the outer circumference. Such a variation in fiber length may be advantageous with respect to fabrication, such as to allow the fiber bundle to be ground and polished to an end profile as a unit.

According to the embodiment of FIG. 7A (aspects also being depicted in FIGS. 7B-7D), the angled face 52a near the top of the fiber bundle 45 provides enhanced light collection efficiency in an area 53a of the field of view away from the centerline 47 and above the upper edge of the fiber bundle 45. Similarly, the angled face 52b below the centerline 47 of the fiber bundle 45 provides enhanced light collection efficiency in an area 53b of the field of view below the lower edge of the fiber bundle. Taken as a whole, the angled faces 52, 52a, 52b thus provide a field of view having greater extent above and below the centerline 47 than would a fiber bundle having a single flat face 50. Similarly, when generated by rotation about axis 47, the angled face 52 as a whole provides higher light collection efficiency across the width and height of a plane normal to the axis 47 having greater extent compared to a flat collection face.

Figure 8:
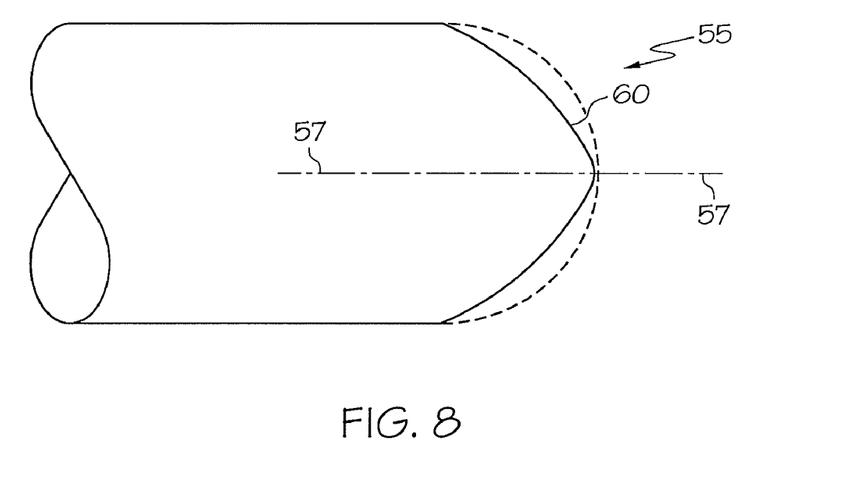
FIG. 8 is a side view of a fiber bundle including a end face having a parabolic surface, according to an embodiment.

In another embodiment shown in FIG. 8, a fiber bundle 55 may have an end face 60 with a parabolic surface. In the embodiment of FIG. 8, individual fibers near the bottom of the fiber bundle 55 have enhanced sensitivity in a direction passing upward across the centerline 57. Similarly, individual fibers near the top of the fiber bundle have enhanced sensitivity in a downward direction. When the fiber bundle 55 is rotated about the axis 57 to form a 3D fiber bundle, the composite effect of fibers ground and polished in a rotationally symmetric parabolic surface 60 (or alternatively in a faceted parabolic surface) is to provide an enhanced collection efficiency in areas of a field of view having greater angular distance from the centerline 57 compared to a flat-ground collection fiber bundle.

Figure 9:
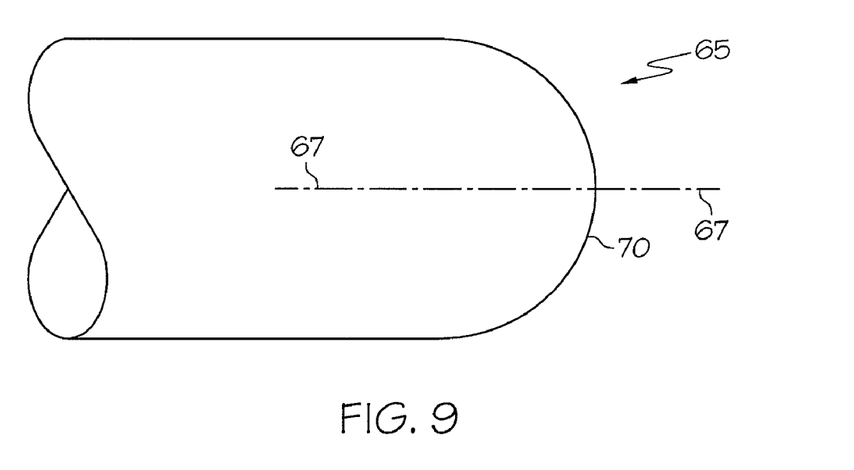
FIG. 9 is a side view of the fiber bundle including a end face having a hemispherical surface, according to an embodiment.

In yet another embodiment as shown in FIG. 9, a fiber bundle 65 may have an end face 70 with a hemispherical surface.

Figure 11:
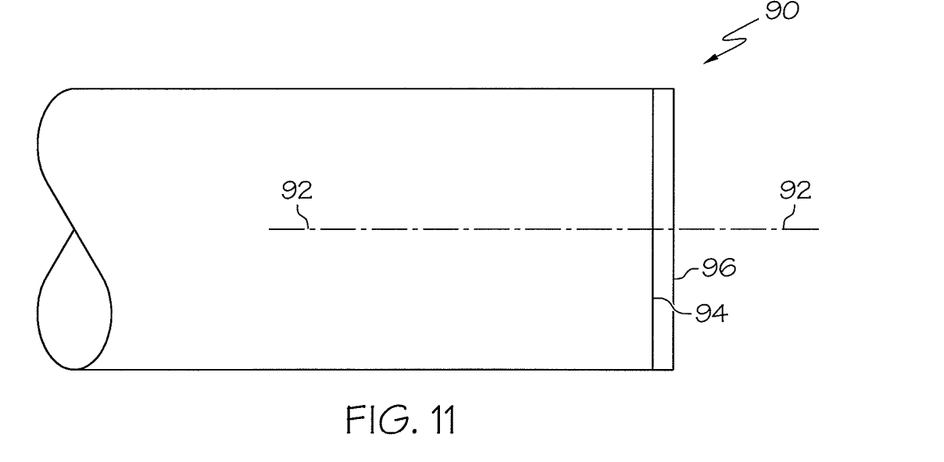
FIG. 11 is a side sectional view of a fiber bundle including a end face coated with a diffusive coating layer, according to an embodiment.

In another embodiment, a fiber bundle 90 end face 94 may have a conventional flat end surface as illustrated in FIG. 11, wherein the end face 94 may be coated with a diffusive coating layer 96. Alternative shapes for end face 94 surface and corresponding diffusive coating layer 96 include but are not limited to multi-faceted surface, parabolic end surface, hemispherical surface, etc. as discussed herein. The diffusive coating layer 96 may contain reflective particles such as titanium dioxide or metallic pigments having a random orientation which act to redirect the incident light into the fiber.

According to an embodiment, the diffusive layer 96 may be comprised of a polytetra-fluoro-ethylene (PTFE) cosine enhancement film.

Figure 12A:
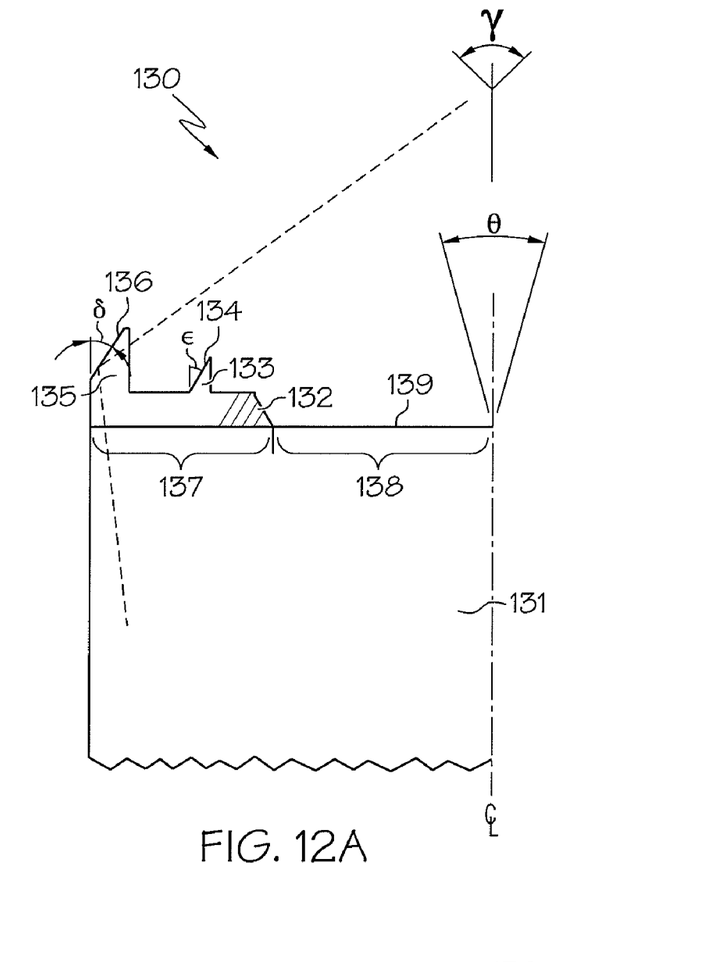
FIG. 12A is a side perspective view of a fiber end face adapted to include a refractive structure having angled ridges, according to an embodiment.
Figure 12B:
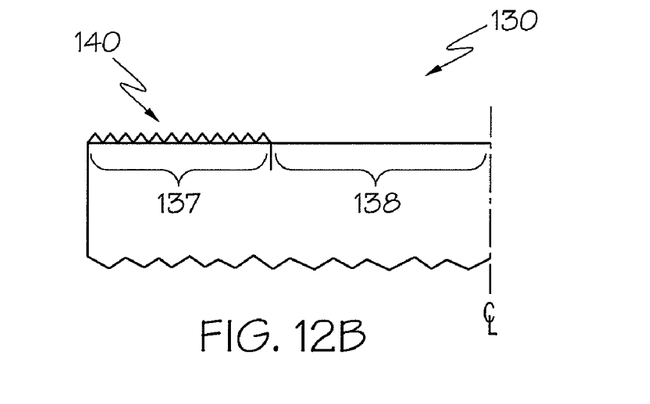
FIG. 12B is a side perspective view of a fiber end face adapted to include a diffractive structure, according to an embodiment.

Pattern-shaping elements may be placed at the end of the fibers as illustrated in FIGS. 12A and 12B. In one embodiment, a fiber end face 130 may be adapted to include a reflective structure 132 as illustrated in FIG. 12A, which shows a radial cross-section of the end of a fiber bundle 131. The radial cross-section may be rotationally symmetric about the central axis of the fiber bundle 131 to form in three dimensions a disk with angled ridges. Angle θ denotes the ordinary acceptance angle determined by the fiber refractive index, its surface 139 and ambient refractive indexes as explained earlier. In one embodiment, angle γ is the increased acceptance angle provided by the invention. The reflective structure 132 is shown by cross-hatched lines and may be characterized as a transparent material having a refractive index no greater than that of the cores of fiber bundles 131. Ridge 133 has back face 134 and ridge 135 has back face 136. These faces 134, 136 are mirrored. Metal may be deposited through a mask to mirror the faces 134, 136 or the entire element 132 may be mirrored and then selectively removed by electron beam ablation or chemical action. Alternatively, the difference in refractive indices between the material of structure 132 and the ambient may provide for total internal reflection at faces 134 and 136 without the need for a reflective coating. The angles δ, ε of the back faces 136, 134, respectively are different so as to collect light from different angular domains. The faces 134, 136 collect radiation within a larger acceptance zone, denoted generally by angle γ. The structure 132 may contain one or more angled ridges. This structure 132 could be made by machining or molding. The structure 132 may be clamped against the polished fiber bundle surface 139 or bonded to it. Radius region 137 may cover the entire bundle or only part of it (i.e., leaving radial region 138 bare). The edge of the structure 132 may be angled as shown and the height of the outermost ridge 135 held to a limited height to avoid shadowing any of the uncovered fibers.

In one embodiment, a fiber end face 130 may be adapted to include a diffractive structure 140 as illustrated in FIG. 12B, wherein the diffractive structure 140 constructed is much smaller than the reflective structure 132 described above. FIG. 12B shows a diffractive coating 140 applied to the face of the fiber bundle 139 in a region 137 with the remainder of the fiber bundle area 138 remaining bare, or treated in some other manner. The diffractive coating 140 may be a homogeneous dielectric thin-film coating without reflective particles deposited on fiber end faces 130 and subsequently treated by a electron beam lithography technique to generate a plurality of diffractive structures (e.g., a grating). Electron beam lithography is a specialized technique for creating extremely fine patterns required by the electronics industry for integrated circuits on silicon wafers. An electron beam scans across the substrate surface and exposes electron sensitive coating. Using methods common in the integrated circuits industry, the shape, sidewall slope, depth and other geometric properties can be controlled to yield a desired shape. Much as in the design of a spectroscopic grating, these shapes can be configured to provide zones of sensitivity well outside the nominal acceptance angle of the fibers as determined by their numeric aperture.

Figure 10A:
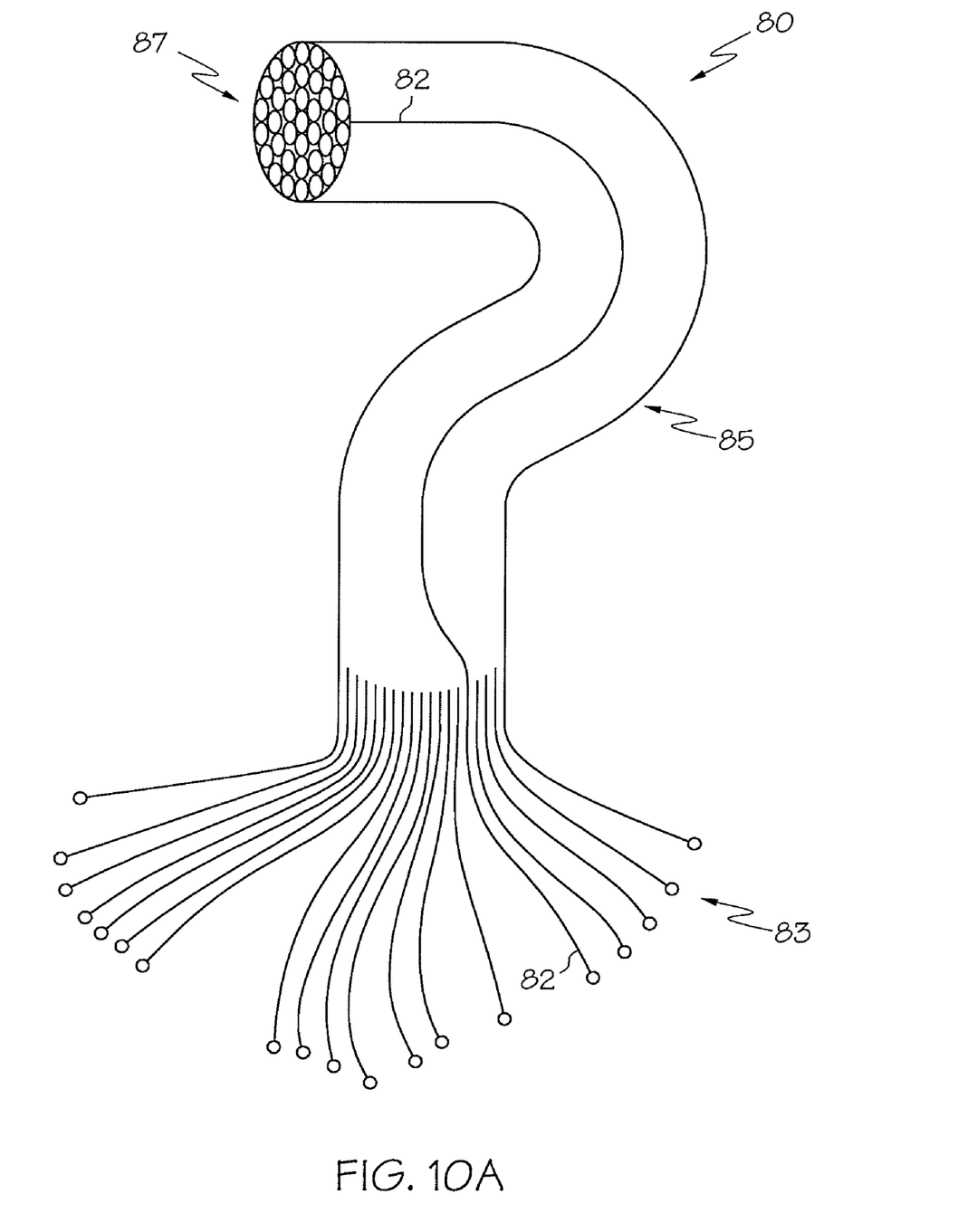
FIG. 10A is perspective view of a light collection bundle where individual receiving fibers are splayed uniformly around a central axis that points in the direction of view, according to an embodiment.

A light collection bundle 80 as illustrated in FIG. 10A includes a receiving end 83, a fiber body 85 and a transmitting end 87. For example, a single fiber 82 within the light collection bundle 80 may receive and transmit light radiation from a region of the field of view. Individual fibers may be uniformly splayed out in different orientations (i.e., at different angles with respect to the central axis of the bundle) within the receiving section 83, and correspondingly may broaden the area of the fiber bundle 80 and may broaden the limits of the cone in which light is accepted in a particular application, such as a particular medical procedure.

Figure 10B:
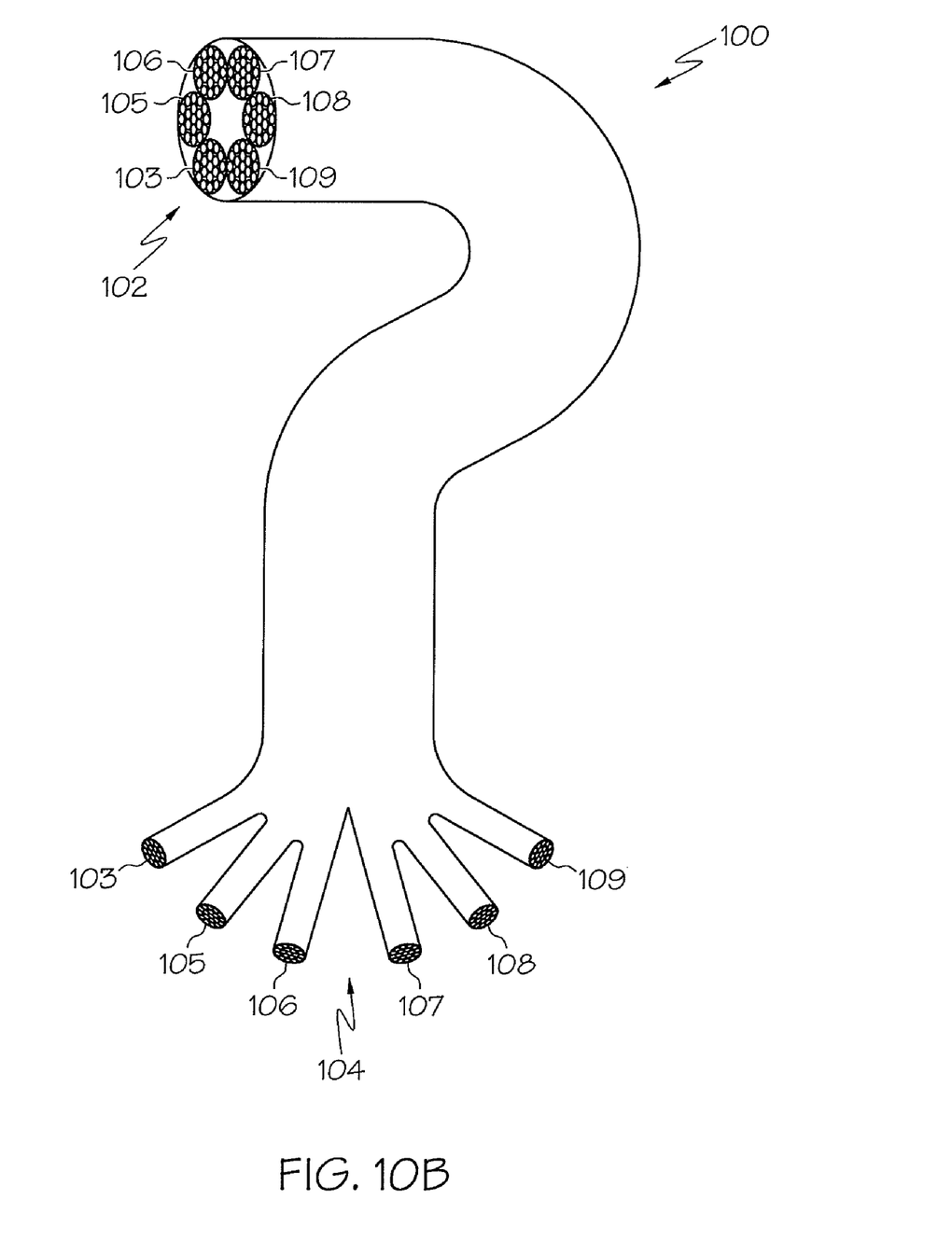
FIG. 10B is perspective view of a light collection bundle where receiving fiber bundles are splayed nonuniformly around a central axis that points in the direction of view, according to an embodiment.

Another light collection bundle 100 as illustrated in FIG. 10B includes a receiving end 104' and a transmitting end. A plurality of fiber groups 103, 105, 106, 107, 108, 109 may be splayed out. Each fiber group 103, 105, 106, 107, 108, 109 may be end-polished perpendicular to a central axis for each cavity 114, 117, 120 (see FIG. 10C). Therefore the fiber bundle end 104 as a whole forms a non-flat surface, but each fiber face is essentially perpendicular to the axes of the respective fiber groups. More or fewer fibers may be assigned to cavities 114, 117, 120, for example to tailor the receiving pattern, thereby controlling the relative sensitivity or light collection efficiency across the field of view.

Figure 10C:
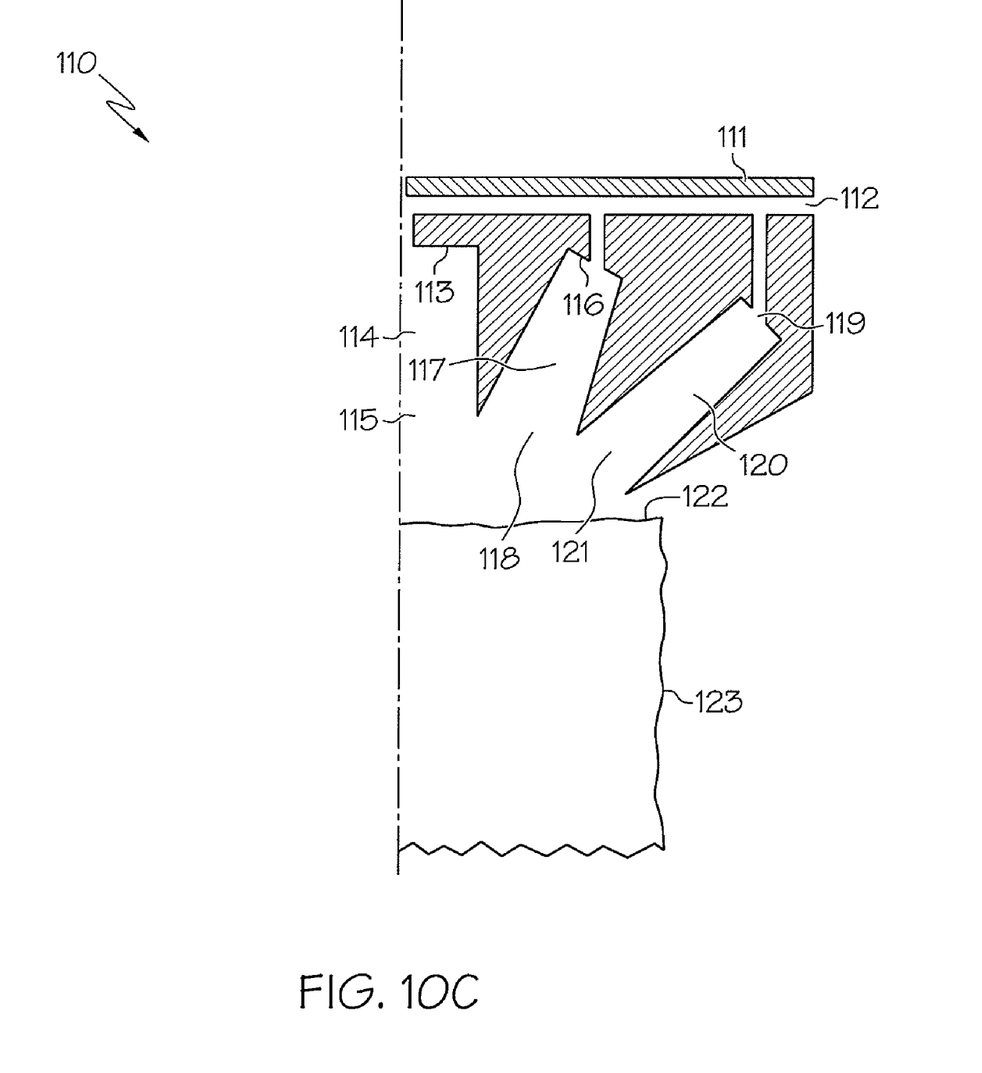
FIG. 10C is a side view of a multi-cavity mold for producing receiving fiber bundles shown in FIG. 10B, according to an embodiment.

In one embodiment, an assembly, generally denoted 110 may be utilized to produce splayed fibers in nonuniform orientations including a mold 111 as illustrated in FIG. 10C. The mold 111 may be rotationally symmetrical as illustrated, however mold symmetry is not necessarily required. The mold 111 may include a plurality of cavities, such as three cavities 114, 117, 120 as illustrated. Cavity 114 is a simple cylindrical void (i.e., area at entrance, 115, and area at end, 113, are equal.) Cavity 117 is a tapered conical void (i.e., area at entrance 118, and area at end 116, are equal but the span of the entrance 118 is greater than the span of the end 116.) Fibers positioned within cavity 117 may adjust their relative position as they are inserted. Likewise, cavity 120 is a tapered conical void (i.e., equal areas but different spans). Fiber bundle 123 is shown approaching mold 111 along the longitudinal axis defined by the centerline of the mold 111. The end of the fiber bundle 122 illustrates the fibers ends roughly aligned. Vacuum 112 may be applied to help draw the fibers into the cavities.

The mold 111 may be constructed from a variety of materials, such as but not limited to plastic, metal and ceramic. The mold 111 may be made by lost wax casting, stereolithography, selective laser sintering, or other conventional means.

An adhesive saturate may be applied to the fiber bundle to fill the spaces within the fibers before insertion into the mold 111. After curing (heat, UV and the like) the entire assembly is machined and polished. Preferably, the top part of the mold 111 is machined away, although in another variation, the top part of the mold 111 may be dissolved away using an appropriate solution. Suitable adhesives include epoxy-polyamide (epoxies), isocyanate-amine (polyureas), isocyanate-polyol (polyurethanes), acrylate copolymer (cyanoacrylates) and polyol-acid (polyesters).

Figure 10D:
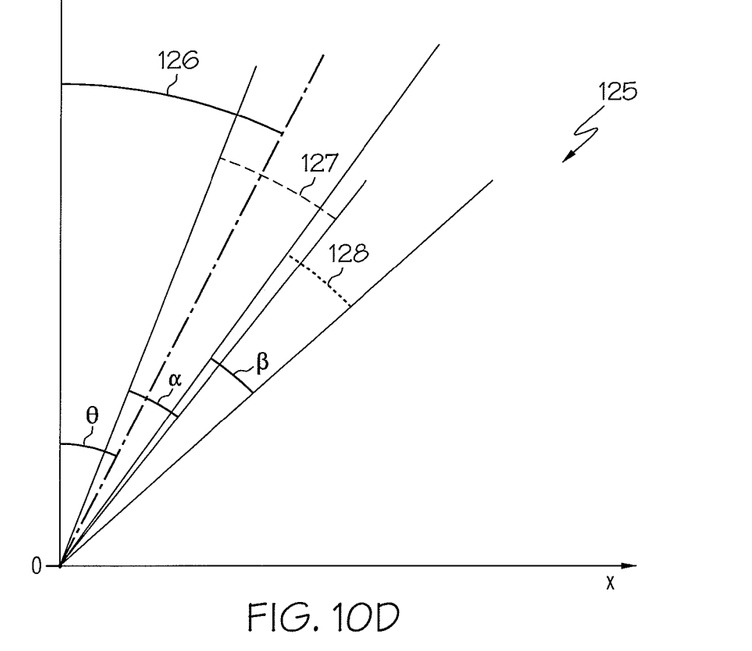
FIG. 10D is a polar plot of the light collection patterns for the receiving fiber bundles shown in FIG. 10B, according to an embodiment.

FIG. 10D illustrates the increased angular range over which the receiving fiber bundle can collect radiation when formed into the shapes enforced by a mold as described above. Curves 126, 127 and 128 are polar representations of the sensitivity of the three angular zones. The curves drawn reflect the efficiency of collection of radiation arriving at the scanning beam assembly from, or along, the direction from a given point on the curve to the origin O. Zero degrees (i.e., x=0) is collinear with the central axis of the light collecting fiber bundle 125. Angle θ is half the ordinary angle of acceptance which has been defined before. The response of the central core 114 (see FIG. 10C) having fiber faces perpendicular to the central axis is shown as curve 126. Curve 127 shows the response of the second zone of fibers 117 (see FIG. 10C) having an inclination to the central axis and an angular extent α. Similarly, curve 128 shows the response of the third outer zone of fibers 120 (see FIG. 10C) having a different inclination to the central axis and an angular extent β. The net angular widths of the response patterns of the zones are determined at least partially by the ordinary acceptance angle and numerical aperture of the fibers. The structure and sensitivity need not necessarily be rotationally symmetric. The central angles and the areas dedicated to each zone may be manipulated to provide a desired net sensitivity pattern.

Figure 13:
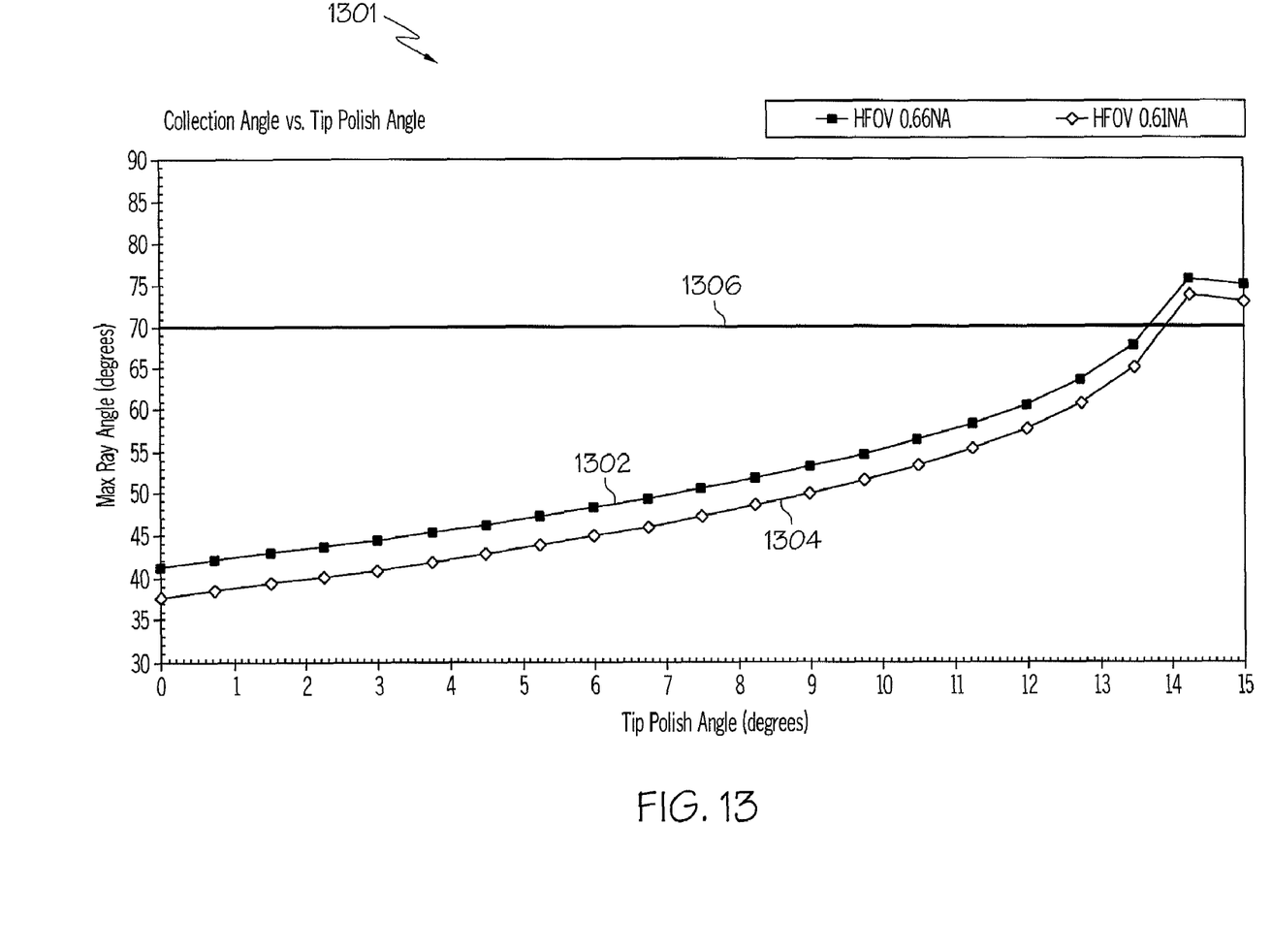
FIG. 13 is a plot of maximum light collection angle as a function of tip angle for two types of collection fibers, according to an embodiment.

FIG. 13 includes plots 1302, 1304 of maximum light collection angles as a function of tip angle for two types of collection fibers, according to an embodiment. The vertical axis of the plot 1301 indicates a desired collection half angle 1306 of about 70 degrees. The vertical axis also indicates the maximum collection angle for fibers having tips angled as indicated by the horizontal axis. A first optical fiber having a collection numerical aperture of about 0.61 is indicated as curve 1304. As may be seen from inspection, multimode collection fibers of the type depicted by curve 1304 may collect light from about 70 degrees off-axis by angling the fiber tip at an angle of approximately about 13.9 degrees. For a multimode collection fiber having a somewhat larger light acceptance angle corresponding to a numerical aperture of about 0.66, the desired about 70 degree half-angle light collection may be achieved by angling the tip of the fiber at approximately about 13.7 degrees.

Figure 14:
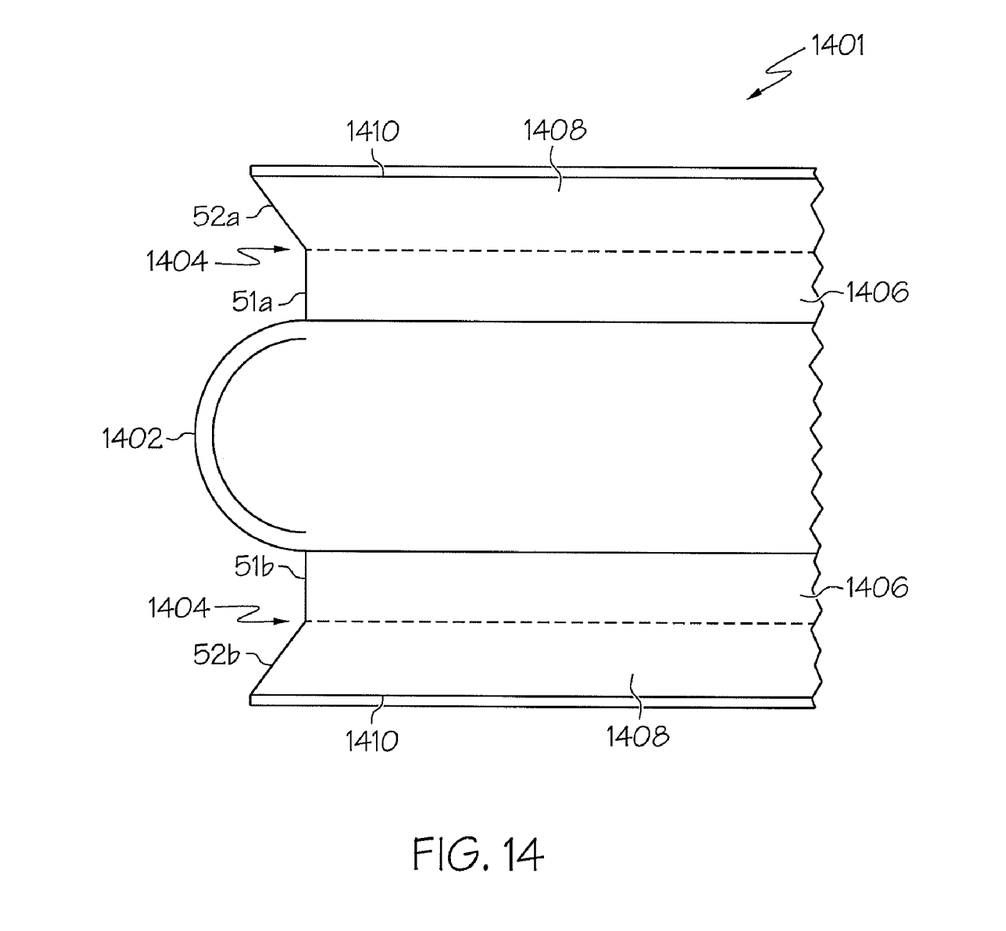
FIG. 14 is a side sectional view of a scanned beam imager tip, according to an embodiment.

FIG. 14 is a side sectional view of the scanned beam imager tip 1401, according to an embodiment. A collection fiber bundle surrounds a beam scanner 1402, terminating in a polished face 1404. A central region of collection fibers 1406 terminates at a flat face 51. A peripheral region of collection fibers 1408 forms an angled face 52. An optional protective sheath 1410 lies peripheral to the assembly. As may be appreciated from the dashed lines separating the collection fiber regions 1406 and 1408, the collection fiber bundle may be formed as a single assembly. The collection surface 1404 of the collection fiber assembly may then be formed into collection surfaces 51*a*, 51*b* and 52*a*, 52*b* using a process such as rotational grinding and polishing, thus creating a differentiation in light collection areas without necessarily having other physical differentiation between the fibers forming the collection surfaces 51 (51*a*, 51*b*) and 52 (52*a*,52*b*). Alternatively, the bundles forming the respective collection regions may be differentiated and assembled together to form the complete collection fiber assembly.

The foregoing description has been presented for purposes of illustration. It is not intended to be exhaustive or limiting and obviously many modifications and variations are possible in light of the above teaching.

What is claimed is:

1. A scanning beam assembly comprising:
a beam generator to generate a beam of radiation;
at least one reflector configured to deflect the beam across a field of view; and
a light collecting fiber bundle including a fiber body which contains a plurality of multi-mode optical fibers and which is disposed for each multi-mode optical fiber to receive radiation reflected from the field of view, wherein the optical fibers have a distal end and a proximal end and the distal end has end surfaces that face in at least two different directions, wherein the fiber body does not contain any optical fiber which is disposed to transmit radiation to the field of view, and wherein the fiber body does not contain any optical fiber which is disposed to directly receive any of the beam of radiation deflected from any of the at least one reflector.

2. The scanning beam assembly of claim 1 wherein the fiber body has a longitudinal axis and includes a first group of fibers that form a core of the light collecting fiber bundle and at least one additional group of fibers that form an annulus surrounding the core.

3. The scanning beam assembly of claim 2 wherein the fibers in the core have end surfaces that face perpendicular the longitudinal axis of the fibers and the fibers in the annulus have end surfaces that face at angles to the longitudinal axis of the fiber.

4. The scanning beam assembly of claim 2 wherein the fibers in the annulus extend further towards the field of view than the fibers in the core.

5. The scanning beam assembly of claim 1 wherein the end surfaces of the fibers in combination form a parabolic surface.

6. The scanning beam assembly of claim 2 wherein the end surfaces of the fibers in the annulus in combination form a parabolic surface.

7. The scanning beam assembly of claim 2 wherein the end surfaces of the fibers in the annulus in combination form a faceted surface.

8. The scanning beam assembly of claim 2 wherein the end surfaces of the fibers in the core in combination form a faceted surface.

9. The scanning beam assembly of claim 2 wherein the end surfaces of the fibers in the annulus in combination form a faceted surface.

10. The scanning beam assembly of claim 2 wherein the end surfaces of the fibers in the core in combination form a multi-faceted surface.

11. The scanning beam assembly of claim 2 wherein the end surfaces of the fibers in the annulus in combination form a multi-faceted surface.

12. The scanning beam assembly of claim 1 wherein the end surfaces of the fibers in combination form a multi-faceted surface.

13. The scanning beam assembly of claim 2 wherein the end surfaces of the fibers in the annulus in combination form a hemispherical surface.

14. The scanning beam assembly of claim 2 wherein the end surfaces of the fibers in the core in combination form a hemispherical surface.

15. The scanning beam assembly of claim 2 wherein the end surfaces of the fibers in the annulus in combination form one or more facets.

16. The scanning beam assembly of claim 15 wherein the facets collect light from different areas of the field of view.

17. The scanning beam assembly of claim 1 wherein the end surfaces of the fibers in combination form a hemispherical surface.

18. The scanning beam assembly of claim 1 wherein the plurality of multi-mode fibers form an end surface and the end surface is coated with a diffusive material that directs light to the end surface from different areas of the field of view.

19. The scanning beam assembly of claim 18 wherein the plurality of multi-mode fibers have end surfaces coated with a diffusive material so as to increase the fiber numerical aperture.

20. The scanning beam assembly of claim 18 wherein the diffusive material is reflective particles.

21. A scanning beam assembly comprising:
a beam generator to generate a beam of radiation;
at least one reflector configured to deflect the beam across a field of view; and
a light collecting fiber bundle including a fiber body which contains a plurality of multi-mode optical fibers each fiber having a distal end and a proximal end and the fiber bundle is disposed for each multi-mode optical fiber to receive radiation reflected from the field of view, wherein the plurality of optical fibers include fibers splayed such that their distal end surfaces face two or more different areas within the field of view to receive radiation from different areas within the field of view, wherein the fiber body does not contain any optical fiber which is disposed to transmit radiation to the field of view, and wherein the fiber body does not contain any optical fiber which is disposed to directly receive any of the beam of radiation deflected from any of the at least one reflector.

22. The scanning beam assembly of claim 21 wherein at least one of the multi-mode optical fibers have an end surface which is coated with a material that directs light to the end surface of the fiber from different areas of the field of view.

23. The scanning beam assembly of claim 21 wherein the light collecting fiber bundle is made up of two or more groups of fibers that extend from the light collecting fiber bundle, wherein each group has an end face that faces an area in the field of view that is different than the areas of the field of view that the end faces of the other groups face.

24. A scanning beam assembly comprising:
a scanned beam generator operable to scan a beam of radiation across a field of view; and
a light collecting fiber bundle which includes a plurality of multi-mode optical fibers each fiber having a distal end and a proximal end, the fiber bundle being aligned to receive scanned radiation scattered from the field of view, wherein the optical fibers have respective distal end surfaces that face in at least two different directions, wherein the light collecting fiber bundle does not include any optical fiber which is disposed to transmit radiation to the field of view, and wherein the light collecting fiber bundle does not include any optical fiber which is disposed to directly receive any of the scanned beam of radiation from the scanned beam generator.

25. The scanned beam assembly of claim 24 wherein the plurality of multi-mode fibers comprises a first plurality of multi-mode fibers having ends cut at a first angle and a second plurality of multi-mode fibers having ends cut at a second angle different than the first angle.

26. The scanned beam assembly of claim 24 wherein the plurality of multi-mode fibers comprises a first plurality of multi-mode fibers splayed to face a first direction and a second plurality of multi-mode fibers splayed to face a second direction different than the first direction.

27. A method for increasing the field of view of a scanned beam imager including at least one reflector configured to deflect a beam of radiation across a field of view, and first and second groups of multi-mode optical fibers, each fiber having a distal end and a proximal end comprising:
scanning a beam of radiation using the scanned beam imager;
collecting radiation from a first region of a field of view with the distal ends a first group of multi-mode fibers; and
collecting radiation from a second region of a field of view different from the first region with the distal ends a second group of multi-mode fibers.

28. A scanning beam assembly comprising:
a scanned beam generator operable to scan a beam of light across a field of view; and
a light collecting fiber bundle which includes a plurality of multi-mode optical fibers disposed to receive light scattered from the field of view, wherein the optical fibers have a distal end and a proximal end and the distal end has end surfaces that face in at least two different directions, wherein the light collecting fiber bundle does not include any optical fiber which is disposed to transmit light to the field of view, and wherein the light collecting fiber bundle body does not contain any optical fiber which is disposed to directly receive any of the scanned beam of light from the scanned beam generator.

* * * * *